(12) United States Patent
Colle (10) Patent No.: US 10,317,195 B2
(45) Date of Patent: Jun. 11, 2019

(54) DEVICE FOR DIMENSIONALLY CHECKING CONTAINERS VIA CONTACTLESS OPTICAL DETECTION

(71) Applicant: TIAMA, Vourles (FR)

(72) Inventor: Olivier Colle, Oullins (FR)

(73) Assignee: TIAMA, Vourles (FR)

( * ) Notice: Subject to any disclaimer, the term of this patent is extended or adjusted under 35 U.S.C. 154(b) by 268 days.

(21) Appl. No.: 15/305,432

(22) PCT Filed: Apr. 14, 2015

(86) PCT No.: PCT/FR2015/051002
§ 371 (c)(1),
(2) Date: Oct. 20, 2016

(87) PCT Pub. No.: WO2015/162357
PCT Pub. Date: Oct. 29, 2015

(65) Prior Publication Data
US 2017/0045352 A1 Feb. 16, 2017

(30) Foreign Application Priority Data

Apr. 22, 2014 (FR) ..................................... 14 53578

(51) Int. Cl.
*G01B 11/12* (2006.01)
*G01N 21/95* (2006.01)
(Continued)

(52) U.S. Cl.
CPC ................ *G01B 11/12* (2013.01); *G01B 5/08* (2013.01); *G01B 5/10* (2013.01); *G01B 5/12* (2013.01);
(Continued)

(58) Field of Classification Search
CPC ...... G01B 11/12; G01B 21/14; G01B 11/002; G01B 11/14; G01B 5/08; G01B 5/10;
(Continued)

(56) References Cited

U.S. PATENT DOCUMENTS

| 3,815,248 A | 6/1974 | Kulig |
| 2002/0078769 A1 | 6/2002 | Giometti |

(Continued)

FOREIGN PATENT DOCUMENTS

| EP | 1 611 965 | 1/2006 |
| FR | 2 965 344 | 3/2012 |

(Continued)

*Primary Examiner* — Hina F Ayub
*Assistant Examiner* — Amanda Merlino
(74) *Attorney, Agent, or Firm* — Clark & Brody (57) ABSTRACT

An inspection device comprises movable equipment (6) driven relative to a stand (7) and fitted with at least one inspection gauge (14, 15). The device also includes a measurement system (30) comprising a contactless transceiver system (30a) for emitting and receiving a light beam (F) along a path in which there is arranged a target (30b) that is securely mounted to the first inspection gauge, the transceiver system being secured to the stand, and delivering measurements continuously of the position of the first inspection gauge relative to the stand (7). A processor unit (31) is provided that means for detecting when the measurements of the position of the inspection gauge delivered by the transceiver system (30a) cease varying, in order to determine that contact has occurred between the inspection gauge and the container.

6 Claims, 7 Drawing Sheets

(51) Int. Cl.
*G01B 21/10* (2006.01)
*G01B 5/12* (2006.01)
*G01B 5/10* (2006.01)
*G01B 21/12* (2006.01)
*G01B 5/08* (2006.01)
*G01B 11/08* (2006.01)
*G01B 21/14* (2006.01)
*G01B 11/00* (2006.01)
*G01B 11/14* (2006.01)
*G01S 17/06* (2006.01)
*G01N 21/84* (2006.01)

(52) U.S. Cl.
CPC ............ *G01B 11/002* (2013.01); *G01B 11/08* (2013.01); *G01B 11/14* (2013.01); *G01B 21/10* (2013.01); *G01B 21/12* (2013.01); *G01B 21/14* (2013.01); *G01N 21/95* (2013.01); *G01S 17/06* (2013.01); *G01N 2021/8455* (2013.01)

(58) Field of Classification Search
CPC .......... G01B 5/12; G01B 21/10; G01B 21/12; G01N 2021/8455
See application file for complete search history.

(56) References Cited

U.S. PATENT DOCUMENTS

2013/0042705 A1    2/2013  Kolmanz et al.
2016/0187165 A1*   6/2016  Leprat .................... G01B 5/08
                                                           33/542

FOREIGN PATENT DOCUMENTS

FR      2 973 107      9/2012
GB      1 432 120      4/1976
JP      08-236923      9/1996

* cited by examiner

DEVICE FOR DIMENSIONALLY CHECKING CONTAINERS VIA CONTACTLESS OPTICAL DETECTION

The present invention relates to the technical field of inspecting hollow articles or containers in the broad sense, such as for example bottles, pots, and flasks, in particular made of glass, for the purpose of detecting dimensional or surface defects, if any, that might be presented by such a container.

In the technical field of inspecting containers, in particular containers made of glass, after the containers have been fabricated, provision is made for performing various inspections in particular of the mouth or the ring of the container (inside/outside diameters, sealing, height), and of the neck of the container (inside diameter, inside profile, broaching).

In order to perform such inspections, it is known to use one or more devices, each having an inspection head for lowering either through an accurate distance depending on the nature of the container, or else until it comes into contact with the container, or indeed to be pressed against the container during the inspection. In conventional manner, such inspection is performed using a machine having either a linear conveyor for holding the containers in accurate positions, or a star container with circular motion that is indexed to place the containers in association with various inspection stations. Each inspection head is moved with reciprocating vertical motion for a star conveyor, whereas for a linear conveyor, the inspection conveyor additionally presents movement that is horizontal.

Patent FR 2 818 748 describes an inspection device having a head mounted on a horizontal slideway that is fastened to a carriage that is moved with vertical reciprocating motion by a belt that is mounted between a free pulley and a pulley driven by a servomotor. One of the drawbacks of such a device is the relatively large mass that is moved, thereby limiting the travel speed of acceleration of the inspection head. It follows that the rate at which containers can be inspected is limited, which constitutes a major drawback in an in-line process for producing containers. Another drawback of such a known device appears when the inspection head is to come into contact with the container. Specifically, since the stroke of the inspection head is undefined, given the dispersion in the heights of containers and the defects that have influence on that stroke, such as those that prevent the inspection head from moving downwards during a broaching operation. Thus, given the undetermined stroke and the onboard mass, a considerable impact can occur between the inspection head and the container, which might damage the container and/or the inspection head. Finally, such a device does not make it possible to determine the origins of detected defects.

Patent GB 1 432 120 describes a device for inspecting containers and comprising a plurality of inspection stations, one of which seeks to determine whether the dimensions of the rings and the necks of containers are acceptable. That inspection station has movable equipment that is driven by a drive system with reciprocating motion relative to the stand of the device in a travel direction that is parallel to the axis of symmetry of the containers. The movable equipment has an outer gauge for inspecting the outsides of the rings of containers and an inner gauge for inspecting the insides of the rings and the necks of containers.

The device described in Document GB 1 432 120 has the same drawbacks as the inspection device described by patent FP 2 818 748.

Also known from French patent application FR 2 174 203 is a machine for inspecting the rings and the necks of containers, the machine having movable equipment driven by a drive system with cyclical reciprocating motion relative to a stand of the machine. The movable equipment is driven in a vertical direction parallel to the axis of symmetry of the containers. The movable equipment has an inspection gauge or template for inspecting the outside of the ring. The template is mounted at the end of a bottom sleeve that is guided to move in reciprocating vertical sliding relative to the stand.

The movable equipment also has a top sleeve mounted coaxially inside the bottom sleeve and provided with a gauge or probe for inspecting the neck. The top sleeve is driven with reciprocating vertical motion to engage the inspection probe inside the neck of the container.

Each sleeve is provided with a collar for passing in a notch of a lever when the template and the probe occupy positions corresponding to a container that is not defective. If the container does not comply with the specified tolerances, then one and/or both of the sleeves will occupy a position in which the collar actuates the lever, thereby operating a switch indicating that the dimensions of the bottle do not comply with the predetermined tolerances.

Such a device makes it possible to know whether a detected defect originates in the neck or the outside of the ring. Nevertheless, such a device does not make it possible to determine the nature of the dimensional defects detected by the probe, such as for example a mouth that is too narrow or too large, or by the template, such as for example a ring that is too large or too small.

However it is important to be able to distinguish between the kinds of defect presented by defective containers in order to be able to act as well as possible on the method of fabricating such containers.

Patent application FR 2 973 107 describes a device for inspecting the dimensions of containers, which device uses a calibration head comprising in particular an outer gauge and an inner gauge. Such a device also has means for detecting a difference in position of the inner gauge relative to the outer gauge, thereby making it possible to characterize a bore defect. The detection means include optical aiming means pointing in a direction perpendicular to the travel of the movable equipment and including a light beam emitter and a receiver cell placed facing each other. The position error of the inner gauge relative to the outer gauge is detected by actuating a target that obstructs or does not obstruct the receiver cell. The cell thus detects the relative position of the gauges when the movable equipment is in its low position, the gauges normally being in maximum contact with the container. Such a device makes it possible to detect bore diameter defects. Nevertheless, such a device does not make it possible to determine that the dimensions of rings and/or necks of containers are acceptable, nor does it enable the various types of defect to be determined for containers having dimensions that are not acceptable, such as height and the inside broaching diameter and the bore diameter and the outside diameter.

Patent application FR 2 965 344 describes an inspection device for the rings and the necks of containers, the device comprising movable equipment driven with reciprocating motion relative to a stand in a travel direction that is parallel to the axis of symmetry of the containers. The movable equipment has an outer gauge for inspecting the outsides of the rings of containers and an inner gauge for inspecting the insides of the rings and the necks of containers. The outer and inner gauges are mounted to be movable independently of each other and relative to the movable equipment in a travel direction parallel to the travel direction of the movable equipment.

Such a device also has a system for measuring the position of the movable equipment relative to the stand in the travel direction. That device also has a system for detecting contact occurring between the inner gauge and the container during the movement of the movable equipment and serving to detect occasions on which contact occurs between the inner gauge and the container. Likewise that device has a system for detecting contact occurring between the outer gauge and the container during the movement of the movable equipment, serving to detect occurrences of contact between the outer gauge and the container. Depending on the position measurements of the movable equipment and on the occurrences of contact between the gauges and a container, the processor unit of that device makes it possible to determine whether the rings and/or necks of the containers are of dimensions that are acceptable and also to determine the types of defects of containers that have dimensions that are not acceptable.

Each system for detecting contact comprises a sensor having one portion secured to the movable equipment and another portion secured to the gauges. The contact sensor thus detects the portions of the sensor being brought to face other at the moment a gauge comes into contact with the container.

The drawbacks of such a device are associated with the sensor being mounted on the movable equipment, which requires an electrical connection to be installed between the onboard sensor and the stationary processor unit. In addition to the drawback associated with the extra weight that needs to be moved, the speeds and the accelerations of the movable equipment impose stresses on the onboard sensor that can weaken it.

Patent application EP 1 611 965 describes a device for inspecting containers, which device has an inspection head carried by a rod driven with reciprocating vertical motion. The rod has a compensation-damper system with a sensor adapted to detect relative movement between the driven rod and the inspection head in order to detect contact being made between the inspection head and the container. Such a device also presents the drawback associated with mounting the sensor on the movable rod.

In the prior art, in the field of soldering components to a circuit, patent application JP H08 236923 discloses a system including a soldering tool that is movable and that is fitted with a contact sensor such as a strain gauge. The system described by that document presents the drawbacks associated with mounting a sensor on the movable equipment.

Likewise, patent application US 2013/042705 describes a device for measuring the thickness of a strip by means of a measurement tip that is maintained in permanent contact on the strip by gravity. A sensor detects the position of the measurement tip, thereby giving information about the thickness of the strip. Such a device does not have a measurement system suitable for detecting occurrences of contact, since in such a device contact is continuous.

The present invention seeks to remedy the drawbacks of the prior art by proposing a device making it possible to inspect the rings and the necks of containers at a high rate in order to verify that the dimensions of the rings and the necks of containers are acceptable, and in order to determine the types of defects that are detected, such a device being robust, accurate, and compact.

In order to achieve such an object, the invention provides an inspection device for the rings and necks of containers, the device comprising:
  movable equipment driven relative to a stand with reciprocating motion in a travel direction parallel to the axis of symmetry of containers and over a maximum stroke, the movable equipment being provided at least with a first inspection gauge for inspecting the rings and/or necks of containers, which gauge is movably mounted relative to the movable equipment in a travel direction parallel to the travel direction of the movable equipment;
  a measurement system for measuring the position of the inspection gauge relative to the stand in the travel direction when contact occurs between the inspection gauge and the container, the measurement system being connected to a processor unit; and
  a processor unit responding to the measured positions of the movable equipment in the event of contact occurring between the gauge and the container in order to determine whether the dimensions of the rings and/or necks of containers are acceptable and to determine the types of defects of containers that have dimensions that are not acceptable.
According to the invention:
  the measurement system includes a contactless transceiver system for emitting and receiving a light beam along a path in which there is arranged a target that is securely mounted to the first inspection gauge, the transceiver system being secured to the stand, and delivering measurements continuously of the position of the first inspection gauge relative to the stand; and
  the processor unit includes means for detecting when the measurements of the position of the first inspection gauge delivered by the transceiver system cease varying, in order to determine that contact has occurred between the first inspection gauge and the container.

The invention also provides an inspection device comprising in combination one or more of the following additional characteristics:
  the movable equipment includes a second inspection gauge, one of the gauges being an "outer" gauge for inspecting the outsides of the rings of containers, while the other gauge is an "inner" gauge for inspecting the insides of the rings and the necks of containers, both gauges being mounted to be movable independently of each other relative to the movable equipment in a travel direction parallel to the travel direction of the movable equipment; the measurement system includes a contactless transceiver system for emitting and receiving a light beam along a path in which there is arranged a target securely mounted to the second inspection gauge, the transceiver system being securely mounted to the stand, and delivering measurements continuously of the position of the second inspection gauge relative to the stand; and the processor unit includes means for detecting when the measurements of the position of the second inspection gauge as delivered by the transceiver system cease varying, in order to determine that contact has occurred between the second inspection gauge and the container;
  the processor unit is connected to a drive system for driving the movable equipment in its reciprocating motion, the processor unit controlling the drive system to cause the movable equipment to move upwards as soon as it is detected that contact has occurred between an inspection gauge and the container;

the system for measuring the position of an inspection gauge is an optical distance sensor that determines measurements of the position of the inspection gauge on the basis of the length of the light path between the target and the transceiver system;

the measurement system determines the length of the light path by a time of flight method or by an interferometry method; and the system for measuring the position of an inspection gauge is an optical position sensor that determines measurements of the position of the inspection gauge of the basis of the position of the target in its measurement field.

Various other characteristics appear from the following description given with reference to the accompanying drawings, which show embodiments of the invention as non-limiting examples.

FIGS. 5A and 5H are section views in elevation showing various configurations of the inspection device corresponding respectively to:

inspecting a bad ring diameter corresponding to a ring that is too large;

a bore and a ring diameter that are correct;

inspecting a bad ring diameter corresponding to a ring that is too small;

a bad bore corresponding to a bore that is too small;

a bad bore corresponding to a bore that is too large;

a bad bore corresponding to a bore with a choked neck;

disengaging the tooling; and detecting that there is no container.

Figure 1:
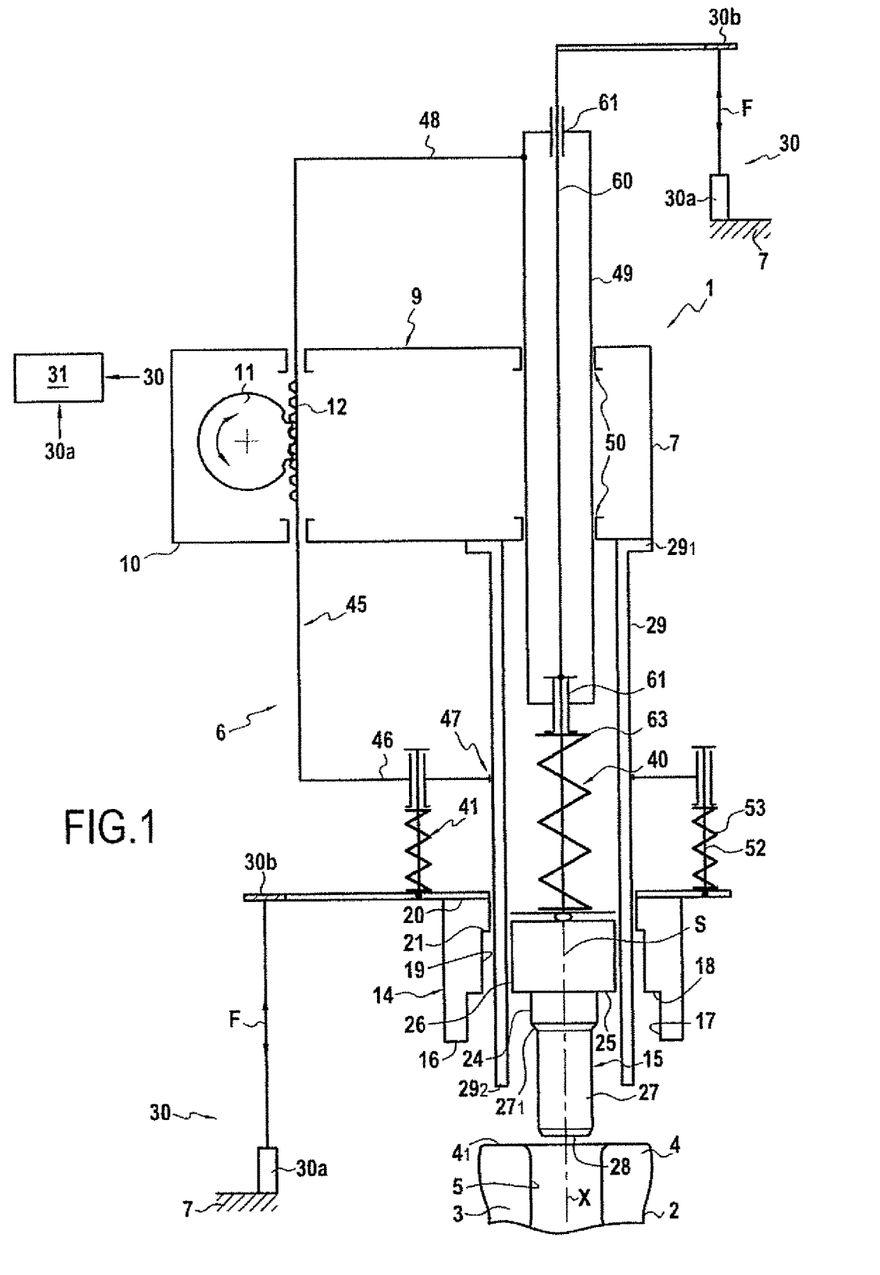
FIGS. 1 and 2 are diagrammatic section views in elevation of the inspection device in accordance with the invention respectively in a disengaged position and in an inspection position, making use of a remote optical sensor.

As can be seen more clearly in FIG. 1, the invention relates to an inspection device 1 for inspecting hollow containers 2 at a high rate, which containers may be of any suitable kind, e.g. being made of glass and presenting an axis of symmetry X. In conventional manner, each container 2 presents a neck 3 having a ring 4 defining the inside of an opening 5 giving access to the inside of the container 2. More precisely, the inspection device 1 serves to inspect the neck 3 and the ring 4 of a container 2 in order to determine whether the rings and necks of containers have dimensions that are acceptable, and in order to determine the types of defects when containers have dimensions that are not acceptable.

The inspection device 1 is for fitting to any machine for producing containers that are delivered at a high rate into register with the inspection device 1 using any appropriate means. The production machine and the means for bringing containers to the inspection device 1 and the means for handling containers are not described since they are well known to the person skilled in the art and specifically they do not form part of the invention. The inspection device 1 is mounted on the frame of an inspection machine incorporated in or fitted to the production machine. In the example shown, it should be observed that the containers 2 are brought into register with the inspection system 1 while in an upright or vertical position, such that the axis of symmetry X of a bottle can be considered as extending in a vertical direction.

The inspection device 1 has equipment 6 that is movable relative to a carrier stand 7. The movable equipment 6 is driven by a drive system 9 for imparting reciprocating motion to the movable equipment along a travel direction parallel to the axis of symmetry X of the containers 2. In the example shown, the movable equipment 6 thus performs for each container 2, both a downward movement and also an upward movement along a vertical travel direction, since the bottle 2 occupies an upright position while it is being inspected by the device 1 of the invention. Naturally, the device 1 is suitable for inspecting bottles placed in other positions.

According to a preferred embodiment characteristic, the drive system 9 comprises a servomotor 10 having its body fastened to the carrier stand 7. The servomotor 10 has an outlet pinion 11 co-operating with a rack 12 that forms part of the movable equipment 6. The servomotor 10 is controlled to turn the outlet pinion 11 in one direction and in the opposite direction so as to impart downward movement and upward movement cyclically along the vertical axis to the rack 12.

The movable equipment 6 includes at least one first gauge for inspecting the rings and/or the necks of containers. The movable equipment 6 preferably includes both a first inspection gauge and a second inspection gauge, with one of the gauges being an outer gauge 14 for inspecting the outsides of the rings 4 of containers, while the other gauge is an inner gauge 15 for inspecting the insides of the rings and the necks of containers 2. As explained in the description below, the gauges 14 and 15 are driven with reciprocating motion by the movable equipment 6 in order to come into contact with a container 2 during the downward movement of the movable equipment 6.

More precisely, the gauges 14, 15 are mounted concentrically, sharing a common axis of symmetry S extending in a vertical direction, so that the in inspection position the axis of symmetry X of the container 2 and the axis of symmetry S are in alignment. On each downward movement of the movable equipment 6 along the vertical axis S, the gauges 14 and 15 inspect the dimensions of the ring and of the neck of the container that is present. The upward movement of the movable equipment is used to enable the inspected container to be removed and the next container to be brought in for inspection.

Figure 5A:
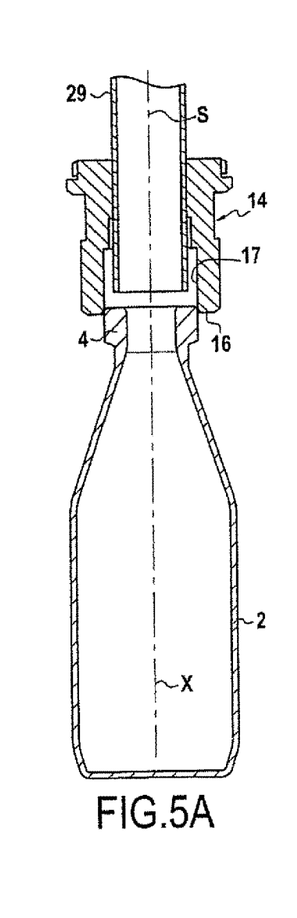

The outer gauge 14 is in the form of a bell of annular shape centered on the axis of symmetry S. The outer gauge 14 presents an "insertion" bottom end 16 defining a calibration opening or bore 17. The inside diameter of this calibration opening 17 is equal to the greatest acceptable diameter for the ring 4 of a container. Thus, as shown in FIG. 5A, if the ring 4 of the container presents a diameter greater than the diameter of the calibration opening 17 (ring too large), then the ring 4 of the container comes into abutment against the bottom end 16 of the outer gauge 14.

The calibration opening 17 is defined by an inside shoulder 18 that is to come into contact pressing against the mouth or rim $4_1$ of the ring 4.

In a preferred variant embodiment, the outer gauge 14 also has an escape bore or opening 19 arranged beyond the shoulder 18, in communication with the calibration opening 17, and leading to the second end 20 of the outer gauge remote from the bottom first end 16. This escape opening 19 is provided with a stop shoulder 21 situated between the second end 20 and the shoulder 18.

Figure 4:
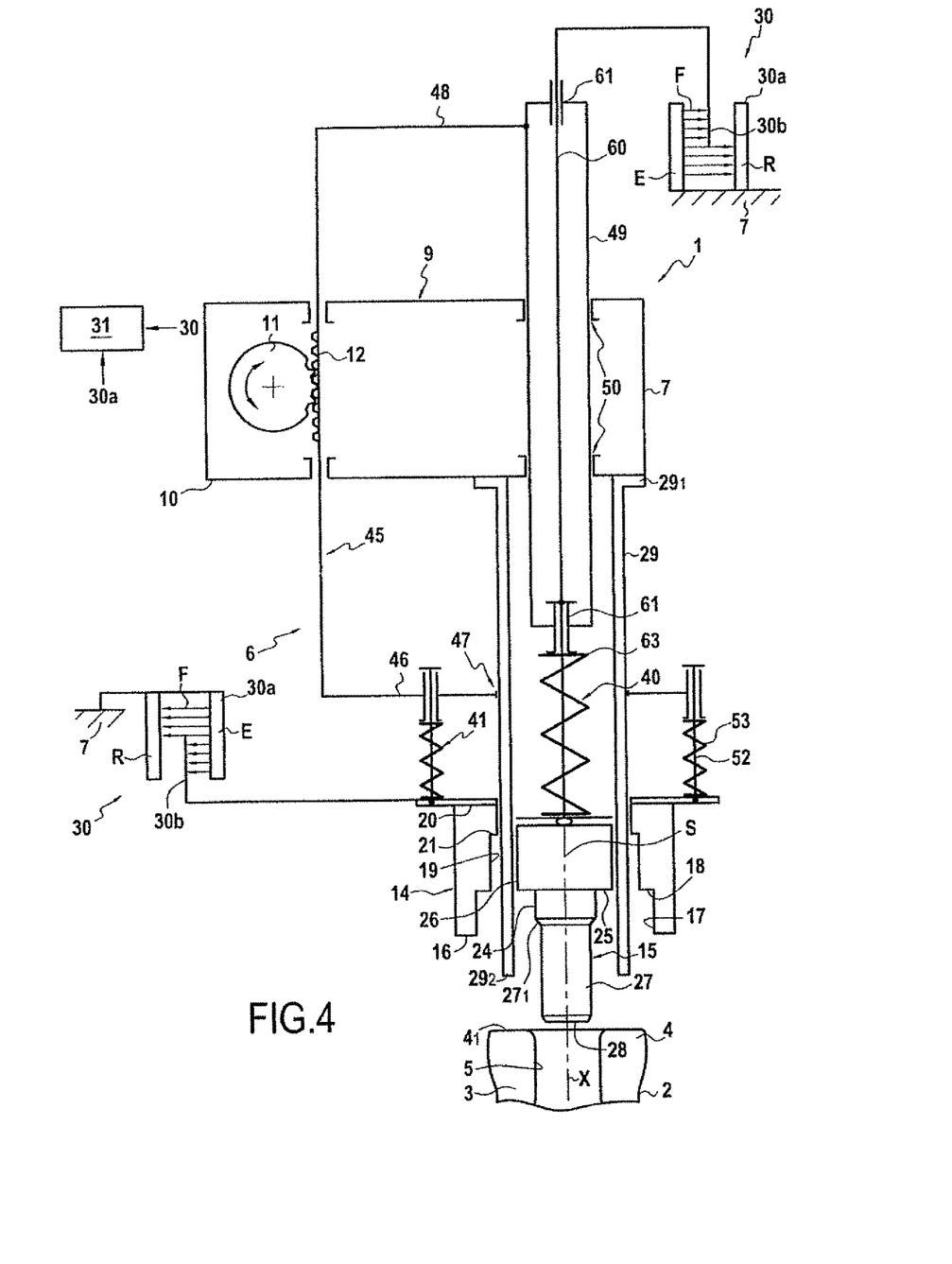
FIG. 4 is a diagrammatic section view in elevation of the inspection device in accordance with the invention, using an optical position sensor.
Figure 5B:
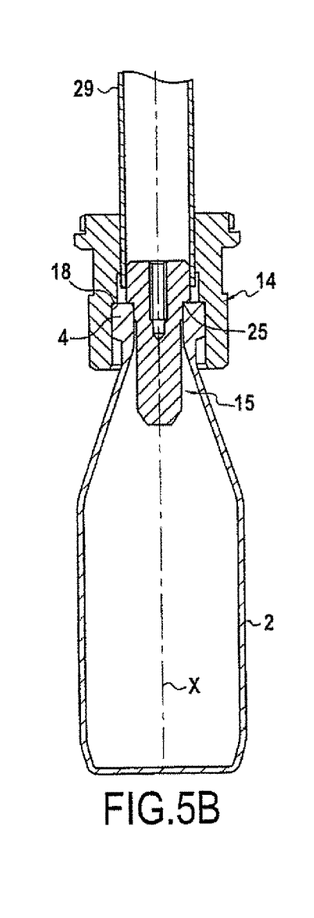

Thus, the calibration opening 17 and the escape opening 19 define between them an annular shoulder 18 of width corresponding to a tolerance range for widths of rings 4 that are acceptable (FIG. 5B). In other words, whenever the ring 4 presents a diameter that is acceptable, then the outer gauge 14 comes to bear via its shoulder 18 against the rim $4_1$ of the ring 4. If the ring 4 presents a diameter smaller than the diameter of the escape opening 19 (FIG. 4C), then the escape opening 19 of the outer gauge 14 receives the ring 4, which then comes into contact with the outer gauge 14 via the stop shoulder 21.

The inner gauge 15 is in the form of a pin or probe mounted inside the outer gauge 14 concentrically with the outer gauge 14. The gauge 15 is symmetrical in shape, being centered on the axis of symmetry S, defining a bottom segment 24 connected via a shoulder 25 to a top segment 26. The diameter of the top segment 25 is greater than the diameter presented by the bottom segment 24. The bottom segment 24 presents a diameter corresponding to the minimum diameter that can be accepted for the mouth of the container 2, while the top segment 26 has a diameter that corresponds to the maximum diameter that can be accepted for the mouth of the container. Thus, the annular shoulder 25, as defined between the top and bottom segments 26 and 24, presents a width that corresponds to the tolerance range for the inside diameter of the neck of the container. When the neck 3 presents a diameter that lies within the tolerance range, then the internal gauge 15 comes into abutment via its shoulder 25 against the rim $4_1$ of the ring (FIG. 5B).

In a preferred variant embodiment, the inner gauge 15 also has an end segment 27 extending from its bottom segment 24 and presenting a diameter that is smaller than the diameter of the bottom segment 24. The end segment 27 possesses a free or abutment end 28 presenting an end segment 27 and in particular via its connection collar $27_1$.

Figure 5C:
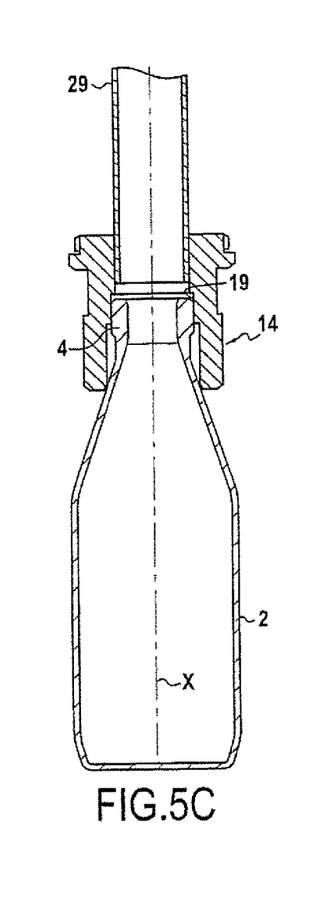
Figure 5D:
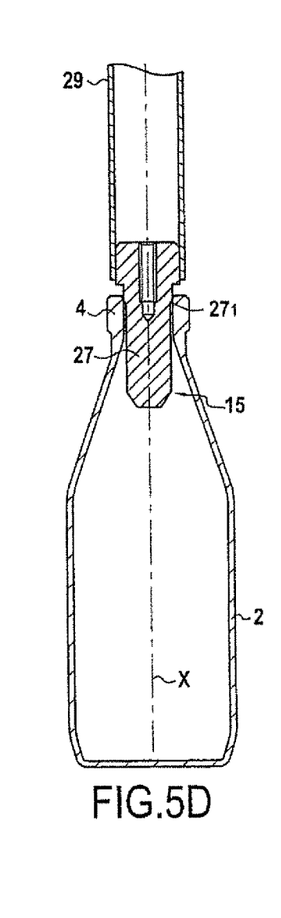
Figure 5E:
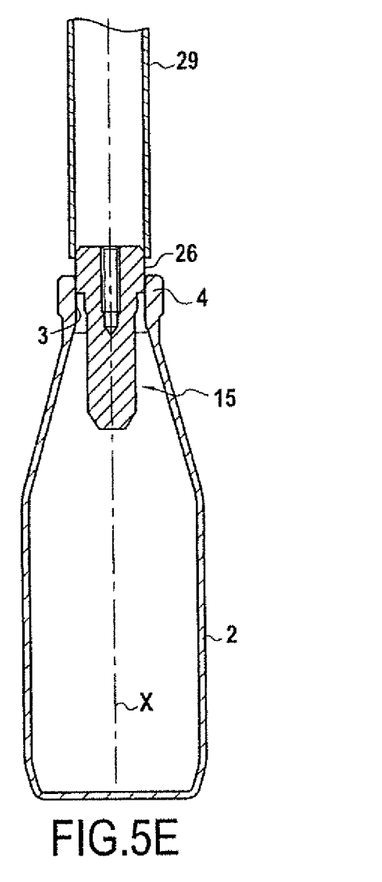
Figure 5F:
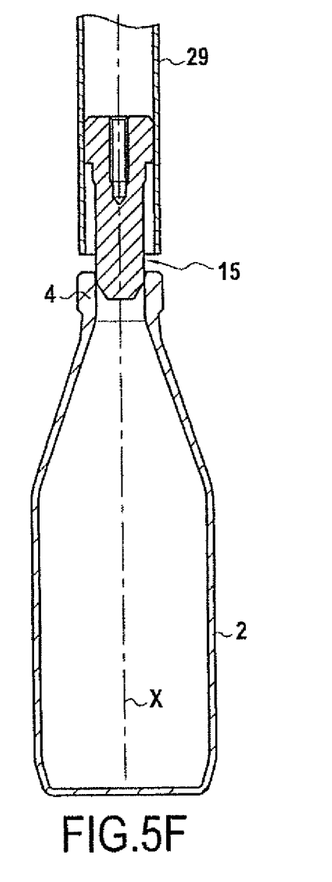

When the neck 3 of the container 2 presents a diameter that is too small, the pin comes into abutment via its end segment 27 and in particular via its connection collar $27_1$ against the container 2 (FIG. 5D). If the inside diameter of the neck 3 is greater than the maximum diameter of the tolerance range, then the top segment 26 penetrates inside the neck 3 of the container (FIG. 5E). Furthermore, when the neck of the container presents a choke defect (FIG. 5F), the inner gauge 15 comes into abutment against the rim of the ring via the end segment 27.

According to a preferred embodiment characteristic, an extractor tube 29 is interposed between the outer gauge 14 and the inner gauge 15. This extractor tube 29 has a first end $29_1$ fastened to the stand 7 so that its longitudinal axis of symmetry coincides with the axis of symmetry S. The extractor tube 29 has a second end $29_2$ remote from the first end $29_1$ and extending between the inner gauge 15 and the outer gauge 14. In other words, the outer gauge 14 extends outside the extractor tube 29, while the inner gauge 15 extends inside the extractor tube 29.

Figure 5G:
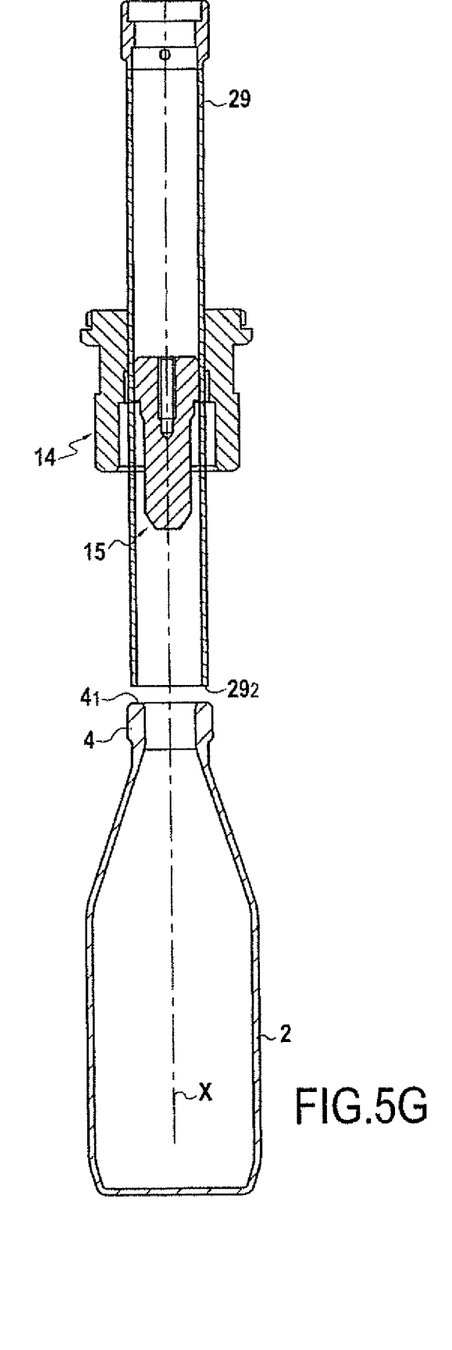

The diameter of the extractor tube 29 is selected to enable it to come into contact with the rim $4_1$ of the ring 4 in the event of the container moving up together with the movable equipment 6, thereby enabling the container to be separated from the movable equipment 6 (FIG. 5G).

It should be observed that the outer gauge 14 and the inner gauge 15 detect each defect at a given level of their travel along the vertical axis that differs from one defect to another. Thus, the inner gauge 15 may for example occupy an altitude that is higher while detecting a choked neck (FIG. 5F) in comparison with the altitude occupied by the inner gauge 15 when it detects a neck having acceptable dimensions (FIG. 5B). Likewise, while detecting a ring diameter that is too large (FIG. 5A), the outer gauge 14 occupies a position at an altitude that is higher than the position occupied by said outer gauge 14 while detecting a ring diameter that is too small (FIG. 5C).

For each gauge 14, 15, the inspection device 1 has a system 30 for contactless measurement of the position of said gauge relative to the stand in the travel direction of the movable equipment when contact occurs between the gauge 14, 15 and the container 2. Such a measurement system 30 thus enables the position of the inner gauge 15 of the outer gauge 14 to be determined relative to the stand 7 (in the vertical direction in the example shown), at least whenever contact occurs between a gauge and the container 2. In other words, such a measurement system serves, for the gauge that is in contact with the container 2, to provide an abscissa value along a distance scale extending in the vertical direction and relative to an origin that is fixed or tied to the stand 7. With the container 2 positioned on a support plane associated with the stand 7, the measurement system 30 gives the position of the gauge 14, 15 relative to the support plane for the container, and consequently relative to the container.

In accordance with the invention, the measurement system 30 includes a transceiver system 30a for emitting and receiving a light beam F along a path having a target 30b, which target is secured to a gauge 14, 15. The transceiver system 30a is secured to the stand 7 and it delivers measurements continuously or permanently relating to the position of the gauge relative to the stand 7. Thus, the transceiver system 30 continuously delivers distance values for each of the gauges 14, 15 relative to the stationary stand 7. In this way, one of the transceiver systems 30a continuously delivers measurements for the position of the outer gauge 14 relative to the stand 7, while the other transceiver system 30a continuously delivers position measurements for the inner gauge 15 relative to the stand 7.

Each measurement system 30 is connected to a processor unit 31 of any conventional type in the form of a microprocessor. Each measurement system 30 thus provides the processor unit 31 with measurements of the positions of the gauges 14 and 15 relative to the stationary stand, i.e. distance values for the gauges 14, 15 relative to a stationary reference frame tied to the stand 7, such as the support plane for the container.

In accordance with the invention, the processor unit includes a system or means for detecting when the position measurements for the gauges 14, 15 as delivered by each transceiver system 30a cease varying. Specifically, when the position measurement of a gauge no longer varies, i.e. when the distance values between a gauge and the stand 7 do not change any more, that corresponds to said gauge coming into contact with the container 2. The processor unit 31 is thus adapted or configured to determine when contact takes place between the inner gauge 15 and the container 2, and also between the outer gauge 14 and the container 2 during the movement of the movable equipment 6.

Furthermore, the outer gauge 14 and the inner gauge are mounted to be movable in the travel direction independently of each other and relative to the movable equipment 6. In other words, it should be understood that each gauge 14, 15 is free to move individually in the vertical travel direction in the event of the gauge making contact with the container 2.

Advantageously, the inspection device 1 includes an "inner" mechanism 40 for damping contact between the container 2 and the inner gauge 15 and for returning said inner gauge to its position. The inspection device 1 also has an "outer" mechanism 41 for damping contact between the container 2 and the outer gauge 15 and for returning the outer gauge to its position. Each damper and return mechanism 40, 41 is thus suitable firstly for damping the contact that occurs between a gauge 14, 15 and the container 2, and secondly for returning each gauge 14, 15 into its initial or rest position in the absence of contact with the container 2.

As can be seen more clearly in FIG. 1, the outer gauge 14 and the inner gauge 15 are mounted to be movable along the travel direction relative to a support 45 of the movable equipment 6. This support 45, which is naturally movable relative to the stationary stand 7, includes the rack 12 having its bottom end secured to a part 46 for holding and guiding the outer gauge 14. This guide part 46 in the example shown is in the form of a plate provided with a hole 47 for passing the extractor tube 29, thus allowing the plate 46 to move vertically in sliding relative to the stationary extractor tube 29. The top end of the rack 12 is secured by a connection part 48 to a guide sleeve 49 extending substantially parallel to the rack 12. This sleeve 49 is guided to slide vertically relative to the stand 7 by guide members 50 of any conventional type. The sleeve 49 is mounted to extend at least in part inside the extractor tube 29.

The support 45 is thus formed by the rack 12, the connection part 48, the sleeve 49, and the plate 46. The outer gauge 14 and the inner gauge 15 are mounted to be movable independently of each other relative to the support 45 and with the help of a respective damping and return mechanism 41 or 40.

Thus, the outer gauge 14 is provided as its damper and return mechanism 41 with at least one guide rod 52 that is mounted to be movable relative to the plate 46 (there being three guide rods in the example shown). Each rod 52 is provided with a return spring 53 interposed between the outer gauge 14 and the plate 46 in order to return the outer gauge 14 to its rest position.

Figure 2:
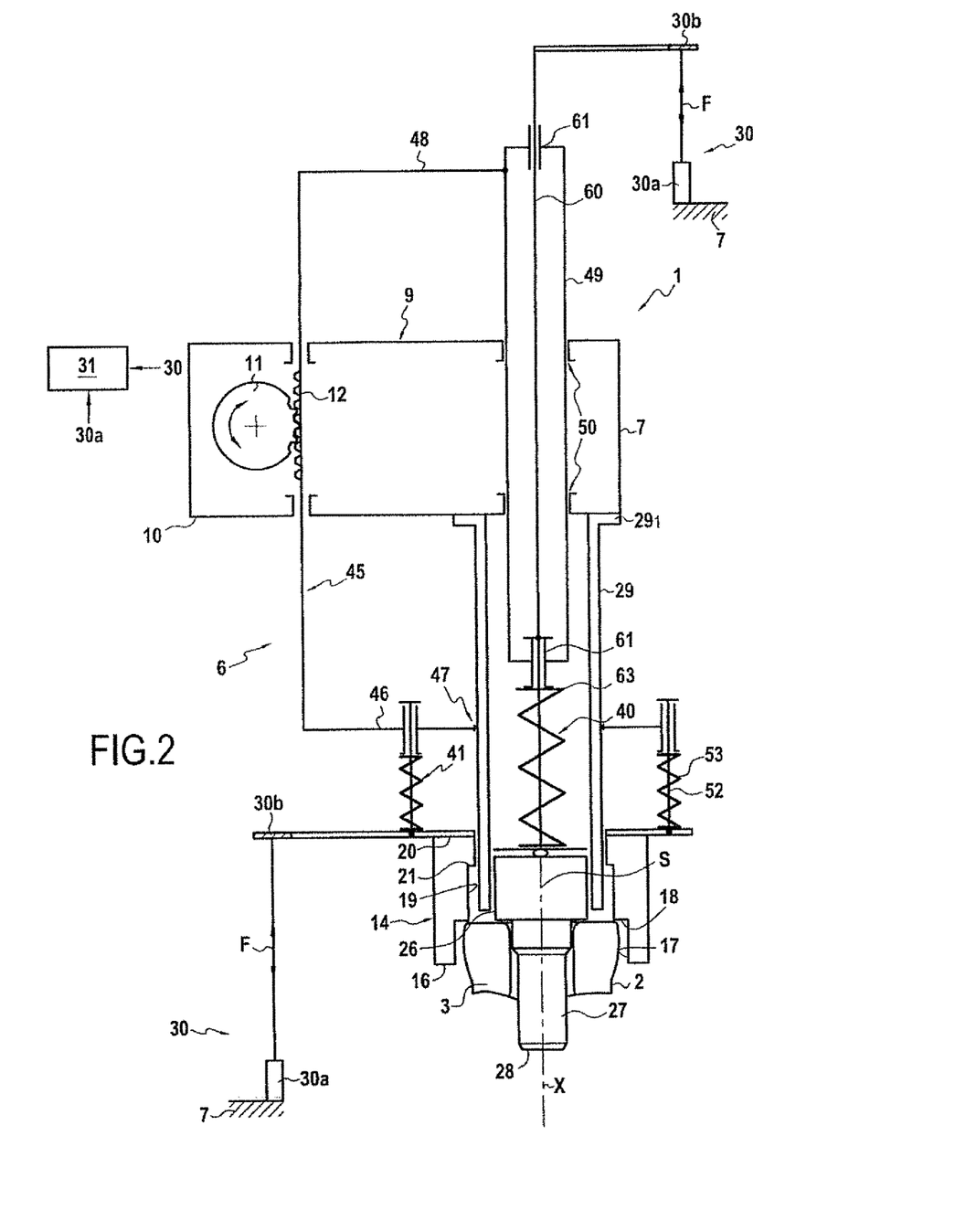

In the absence of contact between the outer gauge 14 and the ring 4 of a container, the outer gauge 14 occupies a rest position relative to the support 45, which position is determined by the return spring 53 and by an abutment carried by the pins 52 and coming to bear against the plate 46 (FIG. 1). When contact takes place between the outer gauge 14 and the ring 4, the outer gauge 14 is subjected to a force causing the outer gauge 14 to move upwards relative to the support 45, thereby compressing the return springs 53 (FIG. 2). When the movable equipment 6 moves upwards, the thrust of the ring 4 against the outer gauge 14 disappears so the return springs 53 cause the outer gauge 14 to return to its initial rest position.

The damper and return mechanism 40 has a rod 60 with a bottom first end secured to the inner gauge 15. The rod 60 is mounted inside the sleeve 49, which acts via any suitable guide means 61 to guide sliding of the rod 60 relative to the sleeve 49.

The rod 60 advantageously includes a spring 63 between the inner gauge 15 and the bottom end of the sleeve 49. In the absence of contact between the inner gauge 15 and the container 2, the spring 63 acts on the inner gauge 15 so as to cause it to occupy a rest position relative to the guide sleeve 49. The rod 60 is held in this position by an abutment carried by the rod and bearing against the sleeve 49 (FIG. 1). In the event of the inner gauge 15 coming into bear against the ring 4, the inner gauge 15 is subjected to a force that causes the rod 60 to rise relative to the guide sleeve 49 (FIG. 2). When the gauge 15 ceases to bear against the ring 4, the spring 63 tends to return the inner gauge 15 to its initial rest position.

In an advantageous embodiment variant, the processor unit 31 is connected to the drive system 9 to control the drive system 9 so as to cause the movable equipment 6 to rise as soon as it is detected that contact has occurred between an inspection gauge 14, 15 and the container 2.

Thus, as soon as an inspection gauge 14, 15 comes into contact with an article 2, regardless of whether it is acceptable or defective, the movable equipment 6 is raised to separate the gauges 14, 15 from the container.

It should be observed that when an inspection gauge 14, 15 is stopped in a given position, i.e. at the moment of contact with a container, the position of the inspection gauge 14, 15 relative to the stand 7 is known from the measurement system 30. It should be recalled that this position of the gauge 14, 15 corresponds to a distance value taken along the travel axis relative to a stationary origin tied to the stand 7.

Naturally, the system 30 for continuously measuring the positions of the inspection gauges 14, 15 relative to the stationary stand 7 and in contactless manner could be implemented in other ways.

In the examples shown in FIGS. 1 and 2, each measurement system 30 comprises an optical distance sensor providing the position measurements for the corresponding inspection gauge 14, 15 on the basis of the length of the light path between the target 30b and the transceiver system 30a. Thus, in order to measure the position of the outer gauge 14, a target 30b is secured to the bell so as to be situated on the path of the light beam F emitted by the transceiver system 30a fastened to the stand 7. In order to measure the position of the inner gauge 15, a target 30b is secured to the rod 60 so as to be situated on the path of the light beams F emitted by a transceiver system 30a fastened to the stand 7.

By way of example, the optical distance sensor 30 is a telemeter having transmitted and reflected light beams that extend in a direction parallel to the travel direction of the movable equipment 6 (FIGS. 1 and 2).

The measurement system 30 determines the length of the light path using a time of flight method or an interferometer method.

Figure 3:
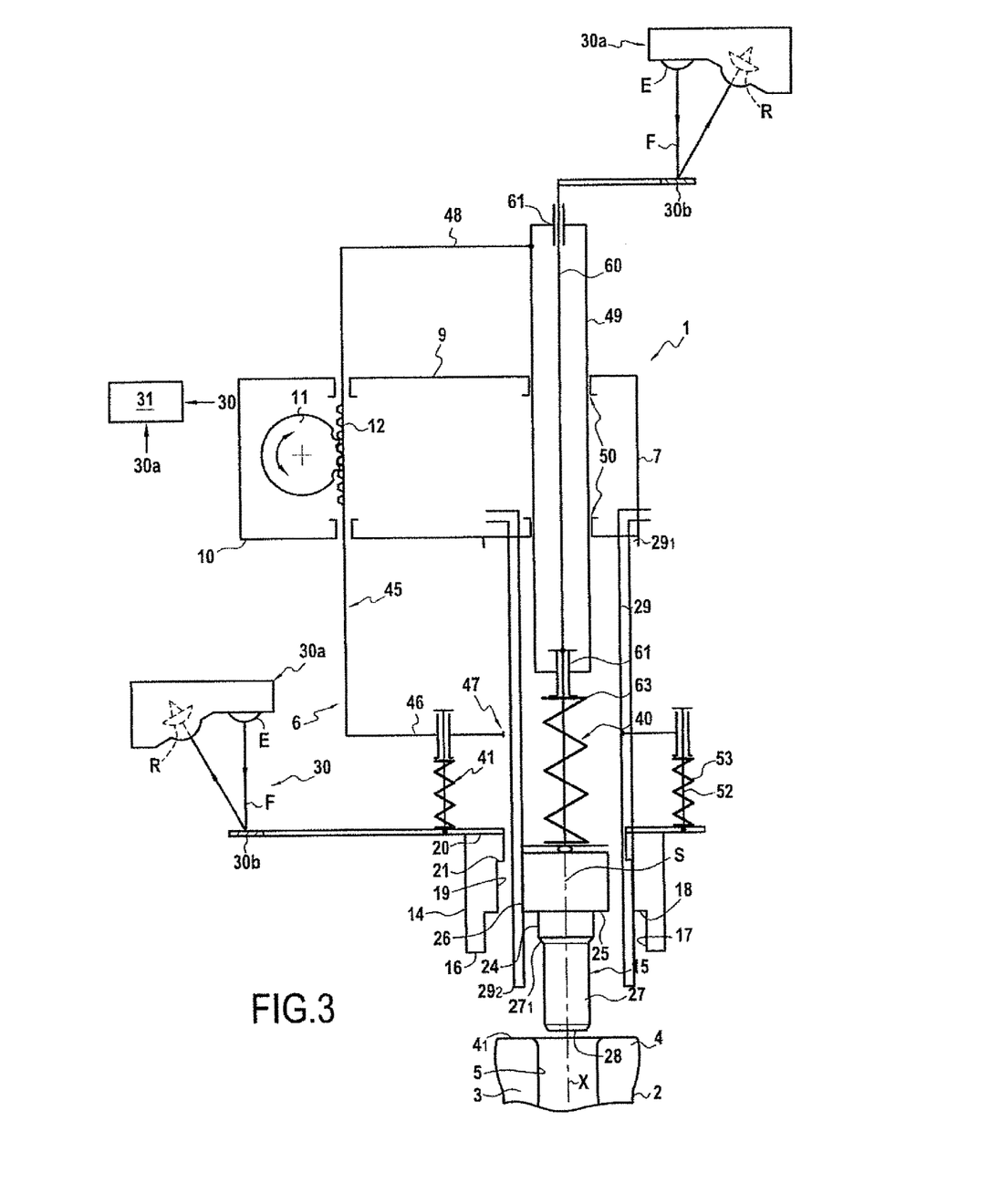
FIG. 3 is a diagrammatic section view in elevation of the inspection device of the invention using a remote optical sensor with triangulation.

As shown in FIG. 3, the light beam F emitted by an emitter E is parallel to the travel direction of the movable equipment 6 and the light beam reflected by the target 30b and received by a receiver R is offset relative to the emitter E. The measurement system 30 determines the position of the target 30b by triangulation.

In the examples shown, the target 30b is made using any appropriate means enabling the optical distance sensor to operate. For example, the target 30b is a portion of a gauge or else a separate light reflector fastened to the gauge.

In another variant embodiment shown in FIG. 4, each system 30 for measuring the position of an inspection gauge 14, 15 is an optical position sensor that measures the position of the corresponding inspection gauge on the basis of the position of the target in its measurement field.

The system 30 for measuring the position of the outer gauge 14 thus includes an opaque target 30b secured to the bell and extending into the light beam F between the emitter E and the receiver R of a transceiver system 30a mounted on the frame 7. The system 30 for measuring the position of the inner gauge 15 has an opaque target 30b secured to the rod 60 and extending into the light beam F between the emitter E and the receiver R of the transceiver system 30a mounted on the frame 7. Naturally, the width of the light beam F in the travel direction of the movable equipment 6 and corresponding to the measurement field of the optical position sensor is not less that the maximum stroke of the movable equipment 6.

The measurement system 30 thus makes it possible to determine the width of the light beam F that is obstructed (or not obstructed) by the opaque target 30b, and consequently to determine the position of the edge of the opaque target 30b along the travel path. The measurement system 30 thus continuously delivers measurements of the position of the inspection gauge relative to the stand 7.

The inspection device of the invention presents the advantage that the position measurement system 30 does not have any active or electrical element mounted on the movable equipment 6, thereby eliminating causes for breaks and complications associated with powering and controlling equipment that is subjected to rapid reciprocating motion. Furthermore, measurement accuracy is very good with optical sensors. Finally, given the good accuracy obtained for the position at which each inspection gauge 14, 15 stops, the inspection system of the invention enables defects to be well discriminated and provides accurate detection of the moment of contact such that the processor unit 31 immediately causes the movable equipment 6 to start moving upwards. The optical sensors used in the invention give satisfaction in practice, unlike ultrasound telemeters, given their characteristics in terms of accuracy or speed.

As mentioned above, each light beam F is created along a length segment that is at least as long as the maximum stroke of the movable equipment 6 in order to make it possible to detect the occurrence of contact along the entire stroke of the movable equipment 6.

On the basis of the measurements delivered by the measurements systems 30, the processor unit 31 can determine whether the rings and the necks of the containers 2 have dimensions that are acceptable. Specifically, each contact position of the gauges 14, 15 corresponds to inspecting a different dimension of the ring and the neck of the container. Using a calibration operation, it is possible to determine the theoretical vertical positions for the gauges 14, 15 that correspond to a container without defect, and consequently the positions that correspond to a container having a defect.

Insofar as the positions of the gauges 14, 15 are known relative to the stand 7, i.e. also relative to the support plate for the containers 2, the processor unit 31 can determine accurately the heights of containers on the basis of contact occurring between the outer gauge 14 and the ring of the container and/or of contact occurring with the inner gauge 15.

The operation of the inspection device 1 stems directly from the above description.

After bringing a container 2 into register with the inspection device 1, the drive system 9 is controlled to lower the movable equipment 6. As soon as a gauge 14, 15 comes into contact with the container 2, that contact is detected by the processor unit 31, which detects that the position of a control gauge ceases varying. At that instant, the processor unit 31 knows from the measurement system 30 the position of the gauge that has come into contact with the container, thus enabling the processor system 31 to determine whether the dimensions of the container are acceptable and to determine the types of defect that are detected for containers having dimensions that are not acceptable. Advantageously, the processor unit 31 also knows from the measurement system 30 responding to either of the two gauges 14, 15 making contact, the position of the movable equipment 6 at the moment a gauge 14, 15 makes contact with the container 2. Using these measurements of the contacts that occur, the processor unit 31 performs calculations providing additional dimensional information about the necks and the rings of the containers 2, and in particular the types of defects that might be presented by the containers 2.

Thus, as a function of the vertical position occupied by each of the gauges 14, 15 relative to the stand 7, and thus relative to the container, when contact is made at least once with the container, the processor unit 31 can determine accurately whether the ring and the neck of the container have dimensions that are acceptable. As explained above, as a function of the vertical position occupied by each of the gauges 14, 15 when contact occurs at least once with the container, the processor unit 31 can determine accurately whether the dimensions of the ring and the neck of the container are acceptable, since it is possible to determine the type of defect from among the following types of defect:
- a defect in which the inside diameter of the neck is less than a minimum acceptable diameter (a plug or choke defect);
- a defect in which the bore diameter is less than a minimum acceptable diameter (a bore defect);
- a defect in which the bore diameter is greater than a maximum acceptable diameter (a bore defect);
- a defect in which the height is greater than a maximum acceptable height;
- a defect in which the height is less than a minimum acceptable height;
- a defect in which the outside diameter is less than a minimum acceptable diameter; and
- a defect in which the outside diameter is greater than a maximum acceptable diameter.

Figure 5H:
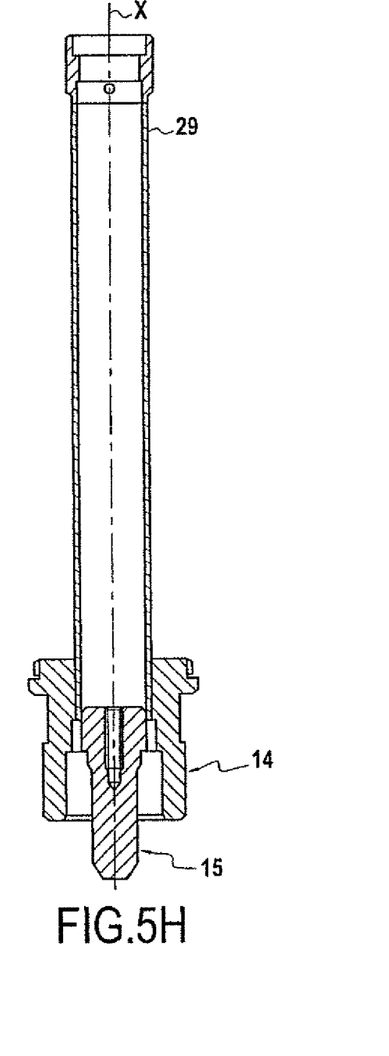

It should be observed that on the basis of contact occurring between one and/or the other gauge 14, 15 and the container 2, the processor unit 31 acts in response to the measured position of the movable equipment 6 to reverse the travel direction of the drive system in order to cause the movable equipment 6 to move upwards. In practice, with containers of acceptable dimensions, the gauges 14, 15 come into contact with the container 2 substantially simultaneously. If there is no container (FIG. 5H), then neither of the detection systems 35, 37 detects contact. The processor unit 31 is suitable for causing the movable equipment 6 to move upwards by controlling the drive system 9 when the movable equipment 6 reaches a previously determined low vertical position.

The invention is not limited to the examples described and shown since various modifications can be made thereto without going beyond its ambit.

The invention claimed is:

1. An inspection device for the rings and necks of containers (2), the device comprising:
   movable equipment (6) driven relative to a stand (7) with reciprocating motion in a travel direction parallel to an axis of symmetry of containers and over a maximum stroke, the movable equipment being provided at least with a first inspection gauge (14, 15) for inspecting the rings and/or necks of containers, which first inspection gauge is movably mounted relative to the movable equipment (6) in a travel direction parallel to the travel direction of the movable equipment;
   a measurement system (30) for measuring the position of the first inspection gauge relative to the stand in the travel direction when contact occurs between the first inspection gauge and the container (2), the measurement system being connected to a processor unit (31); and
   a processor unit (31) responding to the measured positions of the movable equipment (6) in the event of contact occurring between the first inspection gauge (14, 15) and the container (2) in order to determine whether the dimensions of the rings and/or necks of containers are acceptable and to determine the types of defects of containers that have dimensions that are not acceptable;

the device being characterized in that:

the measurement system (30) includes a contactless transceiver system (30a) for emitting and receiving a light beam (F) along a path in which there is arranged a target (30b) that is securely mounted to the first inspection gauge, the transceiver system being secured to the stand, and delivering measurements continuously of the position of the first inspection gauge relative to the stand (7); and the processor unit (31) includes means for detecting when the measurements of the position of the first inspection gauge (14, 15) delivered by the transceiver system (30a) cease varying, in order to determine that contact has occurred between the first inspection gauge and the container.

2. A device according to claim 1, characterized in that:

the movable equipment (6) includes a second inspection gauge (14, 15), one of the first and second inspection gauges being an outer gauge for inspecting the outsides of the rings of containers, while the other of the first and second inspection gauges is an inner gauge for inspecting the insides of the rings and the necks of containers, both first and second inspection gauges (14, 15) being mounted to be movable independently of each other relative to the movable equipment (6) in a travel direction parallel to the travel direction of the movable equipment;

the measurement system (30) includes a contactless transceiver system (30a) for emitting and receiving a light beam (F) along a path in which there is arranged a target (30b) securely mounted to the second inspection gauge, the transceiver system (30a) being securely mounted to the stand, and delivering measurements continuously of the position of the second inspection gauge (14, 15) relative to the stand (7); and the processor unit (31) includes means for detecting when the measurements of the position of the second inspection gauge as delivered by the transceiver system (30a) cease varying, in order to determine that contact has occurred between the second inspection gauge and the container.

3. A device according to claim 1, characterized in that the processor unit (31) is connected to a drive system (9) for driving the movable equipment (6) in its reciprocating motion, the processor unit controlling the drive system (9) to cause the movable equipment (6) to move upwards as soon as it is detected that contact has occurred between the first inspection gauge (14, 15) and the container (2).

4. A device according to claim 1, characterized in that the system (30) for measuring the position of the first inspection gauge (14, 15) is an optical distance sensor that determines measurements of the position of the first inspection gauge (14, 15) on the basis of the length of the light path between the target (2) and the transceiver system (30a).

5. A device according to claim 4, characterized in that the measurement system (30) determines the length of the light path by a time of flight method or by an interferometry method.

6. A device according to claim 1, characterized in that the system (30) for measuring the position of the first inspection gauge (14, 15) is an optical position sensor that determines measurements of the position of the first inspection gauge of the basis of the position of the target in its measurement field.

* * * * *